United States Patent [19]

Hsu et al.

[11] Patent Number: 4,665,266

[45] Date of Patent: May 12, 1987

[54] POLYMER BOUND DEHYDRATION CATALYST AND PROCESS FOR THE PRODUCTION OF DIENES

[75] Inventors: Wen-Liang Hsu, Copley; Neil A. Maly, Tallmadge, both of Ohio

[73] Assignee: The Goodyear Tire & Rubber Company, Akron, Ohio

[21] Appl. No.: 893,845

[22] Filed: Aug. 6, 1986

[51] Int. Cl.$^4$ ................................................ C07C 1/24
[52] U.S. Cl. ..................... 585/606; 502/159; 502/162; 502/167; 585/603
[58] Field of Search ............. 585/606, 603, 607; 502/159, 162, 167

[56] References Cited

U.S. PATENT DOCUMENTS

| | | | |
|---|---|---|---|
| 3,998,864 | 12/1976 | Trevillyan | 502/159 |
| 4,258,206 | 3/1981 | Pittman, Jr. et al. | 502/159 |
| 4,467,118 | 8/1984 | Chalk et al. | 585/603 |
| 4,587,372 | 5/1986 | Hsu | 585/606 |

*Primary Examiner*—Asok Pal
*Attorney, Agent, or Firm*—D. O. Nickey

[57] ABSTRACT

This invention is directed to a process and a catalyst for the conversion of an aldehyde to a diolefin comprising contacting an aldehyde of 4 to 6 carbon atoms in the vapor phase at a temperature of 200° to 300° C. with a polymer bound dehydration catalyst. More specifically, this invention is concerned with a process for the catalytic dehydration of 2-methylbutanal (2MBA) to isoprene in the vapor phase with a polymer bound dehydration catalyst.

10 Claims, No Drawings

POLYMER BOUND DEHYDRATION CATALYST AND PROCESS FOR THE PRODUCTION OF DIENES

TECHNICAL FIELD

This invention relates to a process for the dehydration of aldehydes to dienes. More specifically, this invention is concerned with a polymer bound phosphorous (complex) catalyst for the conversion of 2-methylbutanal (2MBA) to isoprene. The invention is also directed to the catalyst and its preparation.

BACKGROUND ART

Dienes, especially isoprene, are useful as monomers for the manufacture of synthetic rubbers. Isoprene is primarily used to make cis-polyisoprene which is a stereospecific rubber having the same segmeric unit as natural rubber. Several fundamental processes have been used to construct the isoprene $C_5$ skeleton from smaller carbon units. These processes are not commercially accepted in that there are numerous problems associated with each particular synthesis route. One route involves condensing acetylene and acetone followed by hydrogenation and dehydration. Another route involves as a first step the reaction between formaldehyde and isobutylene, and in a subsequent step the intermediate derivative is catalytically cracked at elevated temperatures. See for example, French Pat. No. 1,294,716; Chem. Abstracts 57:15309.

European Patent Application No. 80449 based on U.S. application Ser. No. 315,803 discloses the synthesis of isoprene from linear butenes wherein mixed linear butenes are catalytically isomerized to a mixture of cis- and trans- butene-2, and then hydroformylating the butene-2 mixture to 2-methylbutanal (2MBA) in the presence of a homogeneous rhodium catalyst and organic ligand. The 2MBA is then dehydrated to isoprene in the presence of acidic heterogeneous catalysts at elevated temperatures. This European patent application discloses a preferred catalyst for the dehydration step as a boron phosphate which is described in British Pat. No. 1,385,348. Commercial production of isoprene via the aldehyde dehydration route has not been established since the dehydration catalyst is known to have short lifetimes which limit its utility in commercial applications.

U.K Pat. No. 1,385,348 relates to the conversion of aldehydes to dienes with conjugated double bonds. This British patent recites that particularly preferred acid dehydration catalysts are mixed acid anhydrides, for example, boron phosphate, silicoborate or silicotitanate.

A disadvantage associated with known catalysts to dehydrate aldehydes is that catalyst life depends on many factors which include catalyst composition and structure, catalyst activity, operating temperatures and coke deposition. Coke deposition is understood to denote coke (carbonaceous) deposits formed on the catalyst during the dehydration reaction. As stated earlier, no commercial process based on said technique has been developed so far, since there is no catalyst with selectivity and stability to justify a commercial process.

The use of boron phosphate as a catalyst for the dehydration of alcohols such as 2-butanol and 2-methyl-2-butanol is known. See Jewur and Moffat, *Journal of Catalysis*, 57, 167–176 (1979). The problems associated with an aldehyde dehydration are different and more difficult to overcome than those found in alcohol dehydrations. For example, the boron phosphate dehydration of 2-methyl-2-butanol yields only 2-methyl-2-butene and 2-methyl-1-butene, while dehydration of 2MBA yields primarily methylisopropylketone (MIPK), 2-methyl-2-butene, 2-methyl-1-butene and isoprene. It is the production of the conjugated diolefin, isoprene, that makes the aldehyde dehydrations so difficult, since this highly reactive monomer is known to form dimers and/or polymerize in the presence of acid catalysts.

In addition, aldehydes such as 2MBA are known to undergo aldol condensation. This is a reaction between two molecules of an aliphatic aldehyde whereby a 3-hydroxyaldehyde is formed. Dehydration of the 3-hydroxyaldehyde results in the formation of terpenes, a highly undesirable by-product that can coke and deactivate the catalyst. Due to these and other differences, catalysts suitable for long term dehydration of alcohols have not been found acceptable for aldehyde dehydration.

Regarding the prior art of polymer bound catalysis, there is a general belief by those skilled in the art that all types of polystyrene resins (macroreticular or gel) are inherently thermally unstable both in the presence or absence of oxygen. The upper temperature limit often cited for use of these catalyst-resin systems is quoted at approximately 150° C. See Sherrington "Polymer Supported Reactions in Organic Synthesis"; Chap. 1 p. 27; Wiley: N.Y., 1980; See also: International Workshop on Heterophase Attached Homogeneous Catalysis, Grenoble, France, 1977 (CNRS and NSF) and Chauvin et al, "Polymer Supported Catalysts" Prog. Polymer Sci., Vol. 5, p. 100, Pergamon Press, (1977). The present innovation is concerned with functionalized macroreticular polystyrene that has utility as a catalyst for vapor phase dehydration reactions at temperatures in excess of 200° C.

Substituted phosphines have been used to chemically link a catalyst metal to a polymer support. Examples of this are found in Grubbs et al, "Polymer Preprints," American Chemical Society, Division Polymer Chemistry, 1972, Vol. 13, No. 2, pages 828–832 [Chem. Abs. Vol. 81, 6555d (1974)] and also Grubbs et al, "J. Macromol. Sci Chem.," 1973, Vol. 7, No. 5, Pages 1047–1063, [Chem. Abs. Vol. 78, 164622r (1973)].

U.S. Pat. No. 4,230,633 discloses polymer supported metal complexes wherein the ligand is a cycloalkadienyl radical with metals from Group VIII of the Periodic Table.

U.S. Pat. No. 4,292,415 discloses a crosslinked polystyrene with cycloalkadienyl ligands and Group VIII metal carbonyls.

U.S. Pat. No. 4,323,698 discloses a weak base anion exchange resin which has been contacted with a solution of a coordination compound having at least two ligands connected to at least one central metal atom, to chemically bond the resin to the metal atom by replacement of at least one of the ligands of the coordination compound by a functional group of the weak base anion exchange resin. The complex can be used as a catalyst for hydrogenation, carbon monoxide insertion, polymerization, isomerization, vinyl ester exchange and ethylene oxidation reactions among others.

U.S. Pat. No. 4,144,191 discloses amine resins loaded with bimetallic clusters as novel hydroformylation catalysts. This patent is directed to the conversion of liquid olefins to alcohols in a one-step hydroformylation process which consists of contacting an olefin, such as 1-hexene in the liquid phase, with a gaseous mixture of carbon monoxide and hydrogen and the presence of a catalyst prepared by loading a bimetallic cluster onto an amine resin.

U.S. Pat. No. 4,238,358 discloses the use of anthranilic acid as a ligand for rhodium, palladium, platinum and ruthenium complexes. These catalysts are disclosed as reduction catalysts for liquid phase reactions, i.e. the hydrogenation of olefinic and aromatic hydrocarbons.

The prior art does not disclose or suggest the use of resin phosphorous complex catalysts in vapor phase dehydration reactions. One skilled in this art would readily realize or assume that resins, particularly polystyrene resins would not hold up at the temperatures at which vapor phase dehydration reactions are conducted. See Catalysis, J. R. Anderson and M. Boudant, Eds. Chapter 4; Springer Verlag (1981). One aspect of the present invention is the discovery that the catalysts of the invention can operate at a temperature range from 200° to 300° C.

A portion of the instant invention is directed to a catalyst of high selectivity and low coke deposition in conjunction with extended catalyst lifetimes. The prior art does not suggest or disclose a polymer bound catalyst for the dehydration of aldehydes to dienes which would be suitable for commercial application. The prior art catalyst deactivation can be attributed to coking and possible degradation by water (a by-product of the dehydration). These problems can be limited by binding the catalytic species to a hydrophobic support such as a hydrocarbon polymer or resin.

DISCLOSURE OF THE INVENTION

There is disclosed a process for the conversion of an aldehyde of 4 to 6 carbon atoms to the corresponding diene which comprises contacting the aldehyde in the vapor phase at a temperature of from 200° to 300° C. with a polymer bound phosphorus catalyst, said catalyst is characterized by the formulae IA, IB, II, or III:

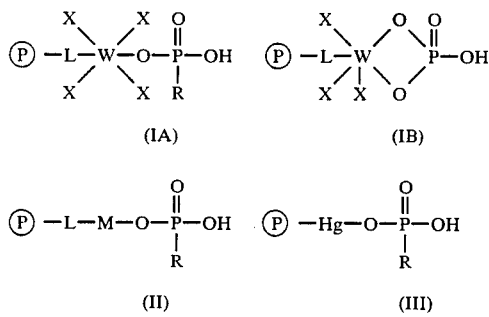

wherein (P) — comprises a styrene-divinylbenzene copolymer;

R is selected from the group comprising hydroxyl, alkyl of 1-12 carbon atoms, aryl or substituted aryl of 6-10 carbon atoms, halogen, haloalkyl, hydroxy alkyl, amine, aminio alkyl, and the radicals:

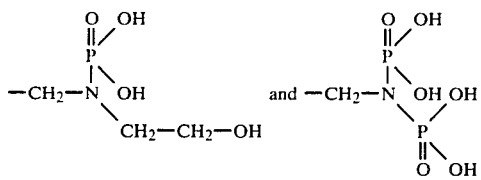

L represents a ligand which is able to bind metals;

M represents a metal selected from copper and palladium; and

X is a radical selected from acetate, chlorine and bromine.

There is also disclosed novel compositions of matter described by the following structural formulae IA, IB, II, or III above;

wherein (P)— comprises a crosslinked macroreticular polystyrene resin which has a crosslink density of at least 4%;

R is selected from the group comprising hydroxyl, alkyl of 1-12 carbon atoms, aryl or substituted aryl of 6-10 carbon atoms, halogen, haloalkyl, hydroxy alkyl, amine, aminio alkyl, and the radicals:

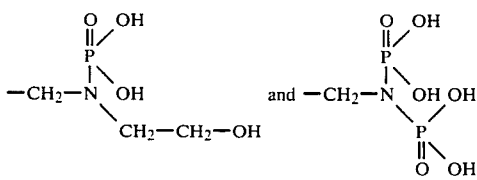

L represents a ligand selected from the group consisting of dipyridyl, 2-aminopyridine, pyridine, 2-amino phenol, 2-imino pyridine and anthranilic acid;

M represents a metal selected from copper and palladium;

X represents a radical selected from acetate, chlorine and bromine.

Further, there is disclosed a heterogeneous catalyst for dehydration reactions conducted in the vapor phase at a temperature from 200° C. to 300° C., said catalyst comprising a catalyst selected from structural formulae IA, IB, II, or III from above.

There is also disclosed a process of preparing isoprene which comprises passing 2-methylbutanal in the vapor phase over a polymer bound phosphorous dehydration catalyst, the improvement comprising the use of a catalyst as described above.

In addition, there is disclosed a process for the conversion of 2-methylbutanal (2MBA) to isoprene which comprises contacting 2MBA in the vapor phase at a temperature of from 200° to 300° C. with a polymer bound metal-phosphorous complex catalyst of structural formulae IA, IB, II, or III as above. The structural formulae presented are the inventors' best estimation as to the atomic relationship; however, the actual catalytic compositions may be mixtures of different reaction products.

Catalysts of structural formulae IA and IB are polymer bound tungsten phosphorous complexes. Due to the metal valence state of tungsten which is 6 for the most stable, two different structures are possible. IA indicates that only one bond forms between the tungsten and the phosphoric or phosphonic acid, while IB indicates that bonds through two of the hydroxyl groups of the acid have formed. It should be appreciated that IA has remaining four -X groups from the tungsten starting material; i.e., tungsten hexachloride, while IB has only 3 remaining. It should also be appreciated that it is possible for more than one phosphoric acid group to bond to the tungsten atom. Lastly, when using tungsten and bidentate ligands, such as dipyridyl, two bonds will form between the ligand and the tungsten atom and thus one less X group will be present.

The polymer bound complexes of this invention are compositions based upon divinylbenzene crosslinked polystyrenes in which the divinylbenzene crosslinking is greater than 4 percent but less than 50 percent. This means that the divinylbenzene crosslinked polystyrenes are prepared with from 4–50% divinylbenzene based on total monomer charge with the remainder being styrene and other monomers (i.e. chloromethylated vinyl benzene). Also, crosslinked polystyrene may be halogenated and then further reacted. Thus, the polystyrene resins starting material useful as a polymeric support in this invention have pendant aryl or chlorobenzyl groups. The representation ⓟ— is meant to stand for the polymer and that the bonding is through the pendant aryl group:

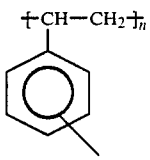

or chloromethylated polystyrene is used, ⓟ— would then represent the polymer and that the bonding is through the pendant benzyl group:

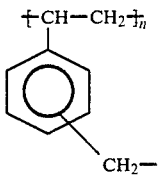

The divinylbenzene crosslinked polystyrene or chloromethylated polystyrene polymer is preferably macroporous or macroreticular in character (i.e. pore size of about 100 to 900 Å). Those skilled in the art are familiar with the manner of obtaining a macroporous polymer rather than a microporous polymer. See Sherrington supra.

Examples of the aldehydes suitable for use in the process according to the invention include 2-methylbutanal, 2,3-dimethylbutanal and 2- or 3-ethylbutanal. 2-Methylbutanal and 2- or 3-ethylbutanal are particularly preferred.

The following materials are mentioned as examples of dienes which can be produced by the process according to the invention: 1,3-butadiene, isoprene, 1,3-hexadiene, 2,3 or 4-methyl-1,3-pentadiene, 2,3-dimethylbutadiene and 2-ethyl-1,3-butadiene.

The process according to the invention is generally carried out at a temperature from 200° to 300° C. with 225° to 275° C. being preferred.

Dehydration of aldehydes by the process according to the invention can be carried out at ambient pressure, for example, by vaporizing the aldehydes and passing them over the catalyst with or without a carrier gas. Inert gases such as nitrogen, carbon dioxide or hydrocarbons, especially saturated hydrocarbons, have proved to be of particular advantage as carrier gases.

The instant invention can also be carried out under reduced pressure, in which case a reduced pressure of from 0.60 to 1.33 Pa below atmospheric pressure has been found acceptable. Compression pressures of from 2 to 10 bar, more particularly from 2 to 4 bar can be regarded as both suitable and adequate.

In the process according to the invention, the aldehyde is passed over the catalyst at an LHSV of at least 2.0, preferably 2.25. By an LHSV of 2.25 is meant 2.25 volumes of liquid aldehyde per volume of catalyst is passed to the preheater for vaporization and then over the catalyst.

It has been found that dilution of the aldehyde feed to the catalyst with a hydrocarbon such as heptane may be advantageous. Dilution of the feed at ratios of 0 to 80% weight percent with an inert hydrocarbon is suitable. Representative of the solvents which are useful for the aldehyde feed dilution are pentane, hexane, heptane, octane, and nonane. One skilled in the art will appreciate that any solvent for the aldehyde which does not interfere with or enter into the dehydration reaction would be appropriate.

An advantage of the process of the instant invention is that the mild reaction conditions enable both the starting material and the reaction product to be sparingly treated, and this is reflected in the high selectivity of the reaction.

The instant invention has proved to be advantageous in that lesser amounts of tar are formed during the dehydration. In the presence of catalysts previously used for aldehyde dehydrations, for example, an aluminum silicate or heretofore used boron phosphates, tar formation occurs to such an extent that after reacting for 30 to 60 minutes there is a substantial decrease in both activity and selectivity of the catalyst. In order to regenerate such coked catalysts, the deposits would have to be burned off and after several regenerations, the catalyst may be totally useless.

Best Mode For Carrying Out The Invention Polymer Support and Ligand Attachment

In one embodiment of the invention, the macroreticular divinylbenzene crosslinked polystyrene polymer is reacted with a ligand to prepare the precursor ⓟ—1— for catalysts of structural formulae IA, IB, and II. Conventionally, a ligand is a molecule, ion, or atom that is attached to the central atom of a coordination compound, a chelate, or other complex. Ligands are also called complexing agents, as for example EDTA, ammonia, etc. In the present invention the ligands are molecules that are attached to the polystyrene polymer through the pendant aryl groups or when chloromethylated polystyrene is used through the pendent benzyl group:

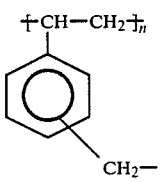

and are capable of complexing with a metal. Ligands such as anthranilic acid or other amines, i.e. 2-aminophenol, are anchored to the polymer by known procedures such as those described by Sherrington supra and by R. J. Card and D. C. Neckers, J. Am. Chem. Soc., Vol. 99, page 7733 (1977).

As used herein, the term "dipyridyl" refers to the 2,2' isomer, which is also known as "bipyridyl".

After attachment of the ligand, the polymer is recovered and then washed with appropriate solvents such as ethanol. The polymer is then slurried in a reaction medium and there is added thereto a metal selected from copper, palladium, and tungsten. After stirring of this slurry for a suitable length of time, the polymer is recovered, e.g. by filtration, and washed and finally extracted to remove unreacted chemicals. The polymer is then reacted with a phosphonic acid or phosphoric acid with the excess acid being washed off before use. Reagent grade phosphoric acid has been found suitable. Phosphonic acids are derived from phosphoric acid wherein one hydroxyl group from the phosphoric acid has been substituted with an alkyl, amine or other radical such as the radical R defined herein. Representative phosphonic acids useful in this invention are phenyl phosphonic acid, methyl phosphonic acid and chloromethyl phosphonic acid.

Polymeric supports in the form of beads, blocks, fibers, spheres, filaments, etc. may be used in the present invention. The use of polymers in the form of beads has been found to be advantageous since the ligand can be incorporated into such beads quite easily. Polymeric beads having a size of about 1 to 10 mm can be suitably employed, although beads having a size as large as 2-5 cm. can also be used with advantage.

Particularly suitable, commercially available polymeric supports useful in the invention are Rohm and Haas XAD-4, Dow Chemical XFS4022 resin and Ionac Resin P-818-1, a chloromethylated polystyrene resin from Sybron Chemical. However, polymeric supports may be easily prepared by those skilled in the art.

Polystyrene polymers can be provided with pendant functionality wherein, for example, anthranilic acid can be anchored to a chloromethylated polymer by a condensation reaction. Examples of such polymers include chlorinated polystyrene in which chlorine atoms can serve as reactive groups and copolymers of styrene with other copolymerizable monomers. In addition, they may be prepared as described in U.S. Pat. No. 2,597,437. Thus, within this context, it is apparent that a wide variety of polymer supports can be used successfully in connection with the preparation of the heterogeneous catalyst of the invention.

The preparation of catalysts of structural formula III do not require the ligation of the resin. Generally, catalysts of structural formula III are prepared from unfunctionalized polystyrene resins by swelling the resin and then reacting with HgO and trifluoroacetic acid.

EXPERIMENTAL

All preparations were carried out under a nitrogen atmosphere. The unfunctionalized polystyrene beads (Dow XFS-4022) were washed with acid, base and organic solvents prior to use. These beads are a macroreticular, highly crosslinked styrenedivinylbenzene (20-30%) copolymers. Trifluoroacetic acid, mercuric oxide yellow and phosphonic acid derivatives were used as received. Phosphorus analyses were performed at The Goodyear Tire & Rubber Company using x-ray fluorescence spectroscopy (XRF).

EXAMPLES I-VI

Preparation of Mercurated Polystyrene-Divinylbenzene Copolymer

Fifty grams of XFS-4022 resin was suspended in 2000 ml of CH$_2$Cl$_2$ at room temperature. To the suspension was slowly added a solution of HgO (52.5 g, 0.243 mol) in trifluoroacetic acid (250 mls) and CH$_2$Cl$_2$ (500 ml). The slurry was stirred 24 hours at room temperature. The resin was then filtered, washed with methanol and vacuum dried at 150° C. for 24 hours.

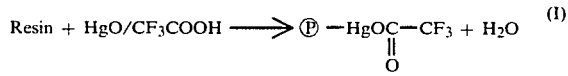

(I)

Preparation of Bound Mercuric-Phosphonic Acid

Fifty grams of the mercurated resin (I) was stirred with 500 ml methanol and the desired amount of phosphonic acid (1-20 mmol) was then added and the mixture was stirred at room temperature for 24 hours. The resin was filtered, washed with methanol and vacuum dried at 150° C. for 24 hours.

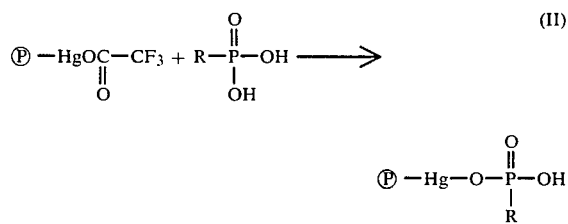

(II)

The prepared catalysts using different phosphonic acid derivatives and their phosphorus analyses are listed in Table 1. They are stable toward moisture and air oxidation.

TABLE I

Phosphorus Analyses* of Polymer Bound Mercurated-Phosphorous Catalysts

| Preparation # Example | Catalyst** | % P by wt. |
|---|---|---|
| I | Ⓟ—Hg—O—P(=O)(OH)—C$_6$H$_5$ | 1.2 |
| II | Ⓟ—Hg—O—P(=O)(OH)—CH$_3$ | 1.5 |
| III | Ⓟ—Hg—O—P(=O)(OH)—CH$_2$Cl | 2.6 |

TABLE I-continued

Phosphorus Analyses* of Polymer Bound Mercurated-Phosphorous Catalysts

| Preparation # Example | Catalyst** | % P by wt. |
|---|---|---|
| IV | P—Hg—O—P(=O)(OH)—CH₂—N[P(=O)(OH)₂]₂ (structure with central nitrogen bonded to CH₂—P(O)(OH)—O—Hg—P and two P(=O)(OH)₂ groups) | 3.0 |
| V | Ⓟ—Hg—O—P(=O)—OH with CH₂—N(CH₂—CH₂—OH)(CH₂—P(=O)(OH)₂) side chain | 1.0 |
| VI | Ⓟ—Hg—O—P(=O)(OH)—NH—C₆H₄—Cl | 1.1 |

*Analyzed by x-ray fluorescence spectroscopy
**Proposed structures

Catalyst Screening and Data Analysis

Reactor System

Dehydrations of 2MBA via polymer bound catalysts were carried out in a reactor system which was a 1.25 cm by 30 cm Pyrex ™ tube and a pump system for delivery of the 2MBA. The reactor also contained a 6 cm by 2 cm preheater filled with Pyrex ™ beads. Three Pyrex ™ thermal wells were situated in the reactor, each fitted with a thermocouple; one in the preheater section, one in the first half of the catalyst bed and one in the lower half of the catalyst bed. The reactor was enclosed with fiberglass heating tapes and wrapped additionally with fiberglass tape. Manual temperature controls were used on the three separate heaters so that each portion was independently heated and controlled. The reactor was thus run under isothermal conditions.

A pump was used to charge the 2MBA feed continuously into the reactor in a downflow manner with a cocurrent nitrogen flow of 14 ml/minute. The effluent from the reactor was passed into a dry ice trap which served as the container for the reaction products. The reactor was run at atmospheric pressure. The nitrogen gas was used as a protective blanket for the catalyst, feed and effluent system. The nitrogen may also serve as a mild diluent and carrier gas although a nitrogen flow as low as 7 ml/minute changed very little in the reaction system.

The liquid hourly space velocity (LHSV) of 2MBA entering the preheater was set at 2.25 for all reactions; however, the LHSV can be varied. LHSV can be defined by more than one set of conditions. Therefore, as used herein, LHSV is the volume of liquid feed per hour that is passed over the total volume of catalyst. Total volume of catalyst is obtained by pouring the catalyst into a graduated cylinder to a mark of, for example, 40 cc's. The LHSV is simply calculated as follows:

$$LHSV = \frac{90 \text{ cc liquid feed/hour}}{40 \text{ cc catalyst}} = 2.25$$

The effluent (dry ice trap) from the reactor was analyzed with a gas chromatograph having a 7 meter column packed with a suitable material for resolving the components in the reaction mixture. Suitable packing materials, such as TCEP on Chromosorb P, are known to those skilled in analytical chemistry. Other conditions of the gas chromatograph were: detector temperature of 210° C., injection port temperature of 210° C., oven temperature program of 3 minutes at 70° C. followed by a 7.5° C./minute rise to 210° C. Standards were prepared and the response factors were determined for isoprene, 2-methyl-2-butene, 2-methyl-1-butene, 2-methylbutanal and methylisopropylketone with nonane as the weighed internal standard.

Since only the organic layer of the reaction effluent was analyzed, the weight of water produced must be calculated from the wt % of isoprene. The following mathematical adjustment was used:

(Wt % Isoprene) (Sample wt) = Wt of Isoprene (Wt % of Isoprene) (18/68) = Wt of Water Sample Wt + Wt of Water = Real Sample Wt (100) (Wt of Water/Real Sample Wt) = Real Wt % of Water Thus, (Wt % Isoprene) (Sample Wt/Real Sample Wt) = Real Wt % Isoprene;

and (Wt % 2MBA) (Sample Wt/Real Sample Wt) = Real Wt % 2MBA;

then

% 2MBA conversion =

$$\frac{(\% \text{ Purity of } 2MBA - \text{Real Wt \% } 2MBA)}{(\% \text{ Purity of } 2MBA)} \times 100;$$

% Isoprene Selectivity =

$$\frac{(\text{Real Wt \% Isoprene} + \text{Real Wt \% Water})}{(\% \text{ Purity of } 2MBA - \text{Real wt \% } 2MBA)} \times 100$$

The 2MBA feed should be at least 90% pure. Other compounds in the 2MBA feed may include various by-products from the reaction of 2-butene and syngas to produce the 2MBA such as 2-methylbutyric acid. Other compounds such as n-pentanal may also be present in minor amounts.

The results obtained from conducting the dehydration reaction with the catalysts set out in Table I are set forth in Table II. The reactor and feed were brought up to the 250° C. reaction temperature and samples of reaction effluent were collected from 3 to 6 hours after the reaction was begun. These samples were analyzed and the data is reported in Table II.

TABLE II

2MBA to Isoprene
Polymer Bound Mercurated-Phosphorous Catalysts
LHSV = 2.25, Neat 2MBA, 250° C.

| Prep/ Ex. # | % Conversion | % Selectivity to Isoprene | % Selectivity to MIBK |
|---|---|---|---|
| I | 67 | 16 | 23 |
| II | 10 | 60 | 0 |
| III | 94 | 3 | 31 |
| IV | 33 | 65 | 6 |
| V | 17 | 80 | 9 |
| VI | 26 | 55 | 5 |

A comparison of catalyst II (R=—CH$_3$) and catalyst III (R=—CH$_2$Cl) evidences that an electron withdrawing group, R=—CH$_2$Cl, tends to make the catalyst more acidic (Bronstead acidity) and catalyze the formation of MIBK.

EXAMPLE VII

Polymer Bound Dipyridyl Tungsten-Phosphorus Catalyst of Structural Formula IB

Twenty-five grams of bound dipyridyl resin and 2.0 g of tungsten hexachloride was stirred at room temperature in 300 ml of absolute ethanol for 20 hours. The light-blue resin beads were collected by filtration and then washed with ethanol and dried. The dried beads were then stirred in a solution containing 200 ml of absolute ethanol and 50 ml of 85% phosphoric acid at room temperature for 20 hours. The light brown beads formed were filtered and washed with 95% of ethanol and dried under vacuum at room temperature for 16 hours. The catalyst contained 2% phosphorous by XRF.

As set above, the tungsten-phosphoric acid catalyst was tested for activity in the dehydration of 2MBA to isoprene. The dehydration was conducted at 275° C. for 24 hours and the percent selectivity and percent conversion were averaged. The percent conversion was 15 while the selectivity to isoprene was 88% and percent selectivity to MIPK was 5.

EXAMPLE VIII

Polymer Bound Dipyridyl Palladium-Phosphorus Catalyst of Structural Formula II

Fifty grams of bound dipyridyl resin were added into a solution containing 3.5 g of palladium acetate in 300 ml of N,N-dimethyl-formamide (DMF). The reaction mixture was then stirred at 70° C. for 1 hours. After cooling to room temperature, the black beads were filtered and washed with DMF and then methanol. The dried beads were then stirred with 50 ml of 85% phosphoric acid in 450 ml of methanol at 80° C. for 16 hours. After cooling to room temperature, the black beads were filtered and washed with methanol and then dried under vacuum at 60° C. for 16 hours. The catalyst contained 4.0% phosphorous by XRF.

The catalyst was tested as described above except at 250° C. The results are set out in Table III.

TABLE III

Polymer Bound Dipyridyl Palladium-Phosphorus Catalyst
250° C., LHSV = 2.25

| Time on Stream | % Selectivity | % Conversion |
|---|---|---|
| 1 | 21 | 42 |
| 2 | 42 | 38 |
| 3 | 42 | 39 |
| 4 | 50 | 32 |
| 5 | 49 | 31 |
| 6 | 51 | 28 |
| 7 | 48 | 29 |
| 8 | 42 | 26 |
| 9 | 42 | 25 |

EXAMPLE IX

Catalysts of Structural Formula II

Polymer Bound Copper-Phosphorous

The resin support for this catalyst was a macroporous partially chloromethylated polystyrene obtained from Sybron Chemical, known as Ionac P-818-1. The resin was dried via azeotropic distillation with toluene and filtered. The resin was then washed, extracted with a CH$_3$OH/THF mixture and finally dried in a vacuum oven at 50° C. The dried resin contained 17.45% Cl by weight. The dried Ionac resin was then reacted with anthranilic acid using the procedure described in U.S. Pat. No. 4,238,358 to give a modified polymer containing 4.44% N and 8.32% Cl by weight. Fifty grams of the anthranilic acid-modified Ionac resin was charged to a 1-liter 3-neck flask along with 14.85 g CuCl and 850 ml DMF. The flask was equipped with a thermometer, nitrogen inlet/outlet, paddle stirrer, heating mantle and temperature controller. The temperature was raised and maintained at 80° C. after the reaction system was flushed with N$_2$. After approximately 24 hours, the reaction mixture was filtered to isolate the resin. The resin was washed with DMF, THF and THF/CH$_3$OH (1/1) then extracted with THF overnight to remove unreacted CuCl. The vacuum dried resin weighed 62.7 gr (25% weight gain). The CuCl/anthranilic acid modified Ionac resin (36 gr) was then reacted in a 3-neck 250 ml flask with a 90 ml H$_3$PO$_4$/90 ml CH$_3$OH mixture at a temperature of 80° C. After 16 hours, the reaction mixture was filtered and the isolated resin was washed and extracted with CH$_3$OH. The air-dried final product weighed 31 gr. Catalysts were screened in a pyrex reactor as previously described. A Milton-Roy pump supplied a constant feed of neat 2MBA to the dehydration system at an LHSV of 2.25. After one hour at 250° C., the temperature of the reactor was raised to 300° C. for 11 hours and then reduced to 275° C.

Samples were taken every 30 minutes and were analyzed by the method previously reported. One reaction product, methyl isopropyl ketone (MIPK), was treated as a starting material for conversion and selectivity calculations. Table IV sets out the conversion and selectivities for this catalyst.

TABLE IV

2MBA to Isoprene
Polymer Bound Anthranilic Acid/CuCl
Treated with H$_3$PO$_4$
300° C., LHSV = 2.25, Neat 2MBA

| Hours on Stream | % Isoprene Selectivity | % Conversion |
|---|---|---|
| 1 | 30 | 5 |
| 2 | 83 | 23 |

TABLE IV-continued

2MBA to Isoprene
Polymer Bound Anthranilic Acid/CuCl
Treated with H₃PO₄
300° C., LHSV = 2.25, Neat 2MBA

| Hours on Stream | | % Isoprene Selectivity | % Conversion |
|---|---|---|---|
| 3 | | 91 | 22 |
| 4 | | 65 | 32 |
| 5 | | 80 | 25 |
| 6 | | 85 | 23 |
| 7 | | 80 | 21 |
| 8 | | 78 | 19 |
| 9 | | 66 | 20 |
| 10 | | 70 | 18 |
| 11 | Temp. dropped | 90 | 14 |
| 12 | to 275° C. | 50 | 11 |
| 13 | | 60 | 10 |
| 14 | | 55 | 10 |
| 15 | | 50 | 9 |
| 16 | | 50 | 9 |
| 17 | | 82 | 6 |
| 18 | | 99 | 5 |

An analysis of the data presented reveals that conversion varied between 14–32% during the 300° C. reaction while isoprene selectivity remained above 65%. Although the catalyst deactivates with time optimization of the ligand and/or metal components may reduce the rate of deactivation and increase isoprene selectivities.

As a control, cupric chloride was supported on alumina and treated with phosphoric acid. Even though the temperature was increased to 350° C., the alumina supported catalyst had only a 25% conversion and 41% selectivity to isoprene after 4 hours, while the polymer bound version above, had a 31% conversion and a 65% selectivity to isoprene after 4 hours on stream. However, both catalysts deactivated similarly.

Polymerization of Produced Isoprene

The reactor effluent from a number of dehydration reactions is purified by distillation and is used as a monomer to produce 1,4-polyisoprene using standard polymerization techniques. The isoprene will polymerize in an acceptable manner and will produce a polymer of expected properties.

Industrial Applicability

As demand for isoprene increases and the supply from petroleum feedstocks decrease, there will be a need for alternative methods of obtaining isoprene. The instant invention provides a process that utilizes a catalyst that overcomes the limitations previously found in the dehydration of 2MBA to isoprene and provides a catalyst that may be modified through ligand, metal and phosphonic acid to meet certain specific conditions and demands. It is the unexpected and unobvious use of a polymer bound phosphate catalyst as described and claimed herein that provides an advancement in the art of converting aldehydes to dienes.

Although the present invention has been described herein with reference to the preferred typical embodiments thereof, it will be apparent to those skilled in the art that there may be modifications made in the process hereof.

What is claimed is:

1. A process for the conversion of an aldehyde of 4 to 6 carbon atoms to the corresponding diene which comprises contacting the aldehyde in the vapor phase at a temperature of from 200° to 300° C. with a polymer bound phosphorus catalyst, said catalyst is characterized by the formulae IA, IB, II, or III:

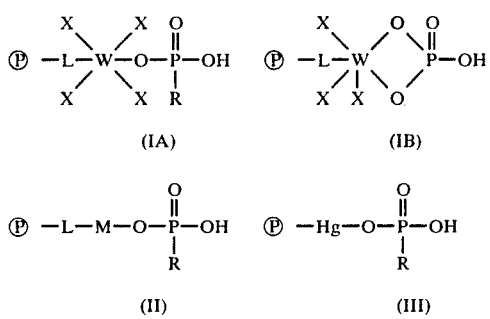

wherein
P— comprises a styrene-divinylbenzene copolymer;
R is selected from the group comprising hydroxyl, alkyl of 1–12 carbon atoms, aryl or substituted aryl of 6–10 carbon atoms, halogen, haloalkyl, hydroxy alkyl, amine, aminio alkyl, and the radicals:

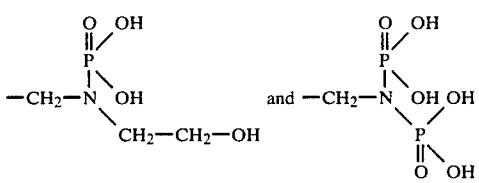

L represents a ligand which is able to bind metals;
M represents a metal selected from copper and palladium; and
X is a radical selected from acetate, chlorine and bromine.

2. A process for the conversion of 2-methylbutanal (2MBA) to isoprene which comprises contacting 2MBA in the vapor phase at a temperature of from 200° to 300° C. with a polymer bound metal-phosphorous complex catalyst of the following structural formulae IA, IB, II, or III:

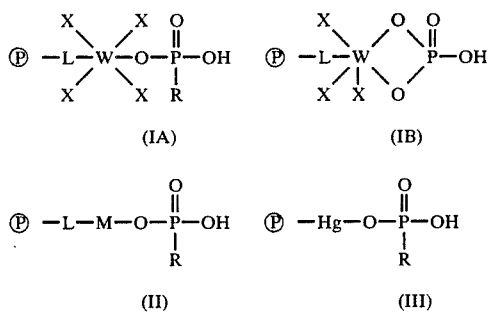

wherein
Ⓟ — comprises a crosslinked macroreticular polystyrene resin which has a crosslink density of at least 4%;
R is selected from the group comprising hydroxyl, alkyl of 1–12 carbon atoms, aryl or substituted aryl of 6–10 carbon atoms, halogen, haloalkyl, hydroxy alkyl, amine, aminio alkyl, and the radicals:

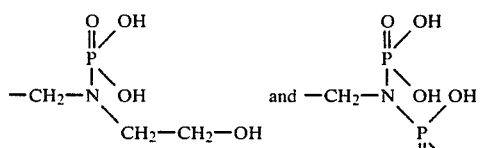 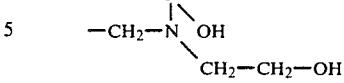

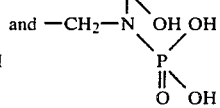

L represents a ligand selected from the group consisting of dipyridyl, 2-aminopyridine, pyridine, 2-amino phenol, 2-imino pyridine and anthranilic acid;

M represents a metal selected from copper and palladium:

X represents a radical selected from acetate, chlorine and bromine.

3. A process according to claim 1 wherein the catalyst of structural formula III is used and R is hydroxyl.

4. A process according to claim 1 wherein the catalyst is of structural formula III and R is the radical:

5. A process according to claim 1 wherein the catalyst is of structural formula II and R is the radical:

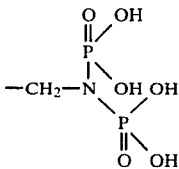

6. A process according to claim 1 wherein the catalyst is of structural formula II and M is copper.

7. A process according to claim 1 wherein the catalyst is of structural formula II and M is palladium.

8. A process according to claim 1 wherein ⓟ— has a divinylbenzene content or crosslinking density of at least 10%.

9. A process according to claim 1 wherein the catalyst is of structural formula IB and L is dipyridyl.

10. A process according to claim 1 wherein the catalyst is of structural formula IA and L is dipyridyl.

* * * * *

UNITED STATES PATENT AND TRADEMARK OFFICE
CERTIFICATE OF CORRECTION

PATENT NO. : 4,665,266

DATED : May 12, 1987

INVENTOR(S) : Hsu et al

It is certified that error appears in the above-identified patent and that said Letters Patent is hereby corrected as shown below:

In Col. 3, at line 63, delete " (P -" and insert therefor -- (P) --.

In Col. 14, at line 19, delete "P-" and insert therefor -- (P) --.

Signed and Sealed this

Twenty-fourth Day of November, 1987

Attest:

DONALD J. QUIGG

*Attesting Officer*          *Commissioner of Patents and Trademarks*